(12) United States Patent
Kawamura

(10) Patent No.: US 7,763,001 B2
(45) Date of Patent: Jul. 27, 2010

(54) ABSORBENT ARTICLE

(75) Inventor: Koji Kawamura, Kagawa-ken (JP)

(73) Assignee: Uni-Charm Corporation (JP)

( * ) Notice: Subject to any disclaimer, the term of this patent is extended or adjusted under 35 U.S.C. 154(b) by 0 days.

(21) Appl. No.: 11/553,114

(22) Filed: Oct. 26, 2006

(65) Prior Publication Data
US 2007/0118090 A1 May 24, 2007

(30) Foreign Application Priority Data
Nov. 18, 2005 (JP) ............................. 2005-335031

(51) Int. Cl.
*A61F 13/15* (2006.01)

(52) U.S. Cl. .................. 604/385.101; 604/385.09; 604/385.28

(58) Field of Classification Search ............ 604/385.19, 604/385.101, 385.24, 385.28
See application file for complete search history.

(56) References Cited

U.S. PATENT DOCUMENTS

| | | | |
|---|---|---|---|
| 5,674,214 A * | 10/1997 | Visscher et al. | 604/385.12 |
| 5,853,403 A * | 12/1998 | Tanzer et al. | 604/385.09 |
| 6,293,935 B1 * | 9/2001 | Kimura et al. | 604/387 |
| 6,646,180 B1 * | 11/2003 | Chmielewski | 604/368 |
| 6,716,204 B1 * | 4/2004 | D'Acchioli et al. | 604/385.19 |
| 6,955,667 B1 * | 10/2005 | Tanaka et al. | 604/385.24 |
| 2001/0021836 A1 * | 9/2001 | Kashiwagi | 604/385.24 |
| 2005/0267436 A1 * | 12/2005 | Mishima et al. | 604/385.19 |

FOREIGN PATENT DOCUMENTS

| | | |
|---|---|---|
| EP | 1051957 A2 | 11/2000 |
| JP | 09-313529 | 12/1997 |
| JP | 10-272152 | 10/1998 |
| JP | 2001-224628 | 8/2001 |
| JP | 2002-320638 | 11/2002 |
| JP | 2003-010240 | 1/2003 |
| JP | 2004-008507 A | 9/2009 |
| WO | 02/100315 A | 12/2002 |

OTHER PUBLICATIONS

International Search Report of PCT/JP2004/018273 issued Apr. 26, 2005.
Extended European Search Report issued to EP Application No. 06811129.3, mailed Jul. 14, 2009.

* cited by examiner

*Primary Examiner*—Tatyana Zalukaeva
*Assistant Examiner*—Lynne Anderson
(74) *Attorney, Agent, or Firm*—Lowe Hauptman Ham & Berner, LLP

(57) ABSTRACT

An absorbent article includes a fluid permeable top sheet, a fluid impermeable back sheet, and an absorbent body disposed therebetween, and in addition is provided with an evagination means extending in a longitudinal direction between the top sheet and the back sheet. The top sheet has a first attachment region attached to the evagination means, second attachment regions attached to the vicinity of both side edges of the absorbent article, and an unattached region positioned between the regions. In the unattached region, many inflected creases, in particular, diagonally directed creases directed from the first attachment region towards both side edges are generated.

20 Claims, 5 Drawing Sheets

ABSORBENT ARTICLE

This application is based on and claims the benefit of priority from Japanese Patent Application No. 2005-335031, filed on 18 Nov. 2005, the content of which is incorporated herein by reference.

BACKGROUND OF THE INVENTION

1. Field of the Invention

The present invention relates to an absorbent article having fluid absorbent capability, and in particular relates to an absorbent article suitable for use as a urine collection pad.

2. Related Art

A urine collection pad is provided for incontinence but modes of incontinence are not uniform. Various forms of incontinence may be envisaged, from incontinence in which large quantities of urine are discharged, to incontinence in which only a small amount of urine is excreted. For example, since slight incontinence, which occurs with abdominal pressure due to sneezing or the like, results in only a little urine excretion, the urine is not excreted from the urinary tract with force, but moves easily on the skin. As a result, if the urine collection pad and the excretion area of the body are not in close contact, the urine that moves on the skin cannot move assuredly to an absorbent body, and leaks easily to outside the urine collection pad. Furthermore, with urgent incontinence, a relatively large amount of urine is excreted at one time. In such cases, if the urine is not quickly absorbed by the absorbent body, it is in contact with the skin for a long period, so that skin roughness easily occurs, and there is a risk of leakage occurring. Therefore, there is a need to rapidly absorb the urine, even when the amount thereof is large.

In this way, the absorbent article used as the urine collection pad must be able to rapidly and assuredly absorb urine, whether excreted in small amounts or in large amounts. This is the same for an absorbent article used as a sanitary napkin.

In generally, the absorbent article used as the urine collection pad is composed of a fluid permeable top sheet, a fluid impermeable back sheet, and an absorbent body positioned between the top sheet and the back sheet, and the absorbent body is formed by mixing pulp and highly absorbent fiber. Technology for capturing a small amount of urine is disclosed for absorbent articles described in, for example, Japanese Patent No. 3442929 and Japanese Unexamined Patent Application Publication No. 2002-320638.

These absorbent articles are formed with bossing extending in a longitudinal direction on a fluid-receiving surface that is in contact with the body of a wearer. Since the bossing portion can be in close contact with the excretion area of the wearer, small amounts of urine excreted by the excretion area can be easily trapped.

However, as in the absorbent articles described in Japanese Patent No. 3442929 and Japanese Unexamined Patent Application Publication No. 2002-320638, the bossing portion itself, formed on a fluid absorbent sheet, is in direct contact with the skin, and when body fluid such as urine is initially absorbed, if the body fluid is excreted in a large amount, the large amount of fluid can easily remain on both sides of the bossing portion. Furthermore, the urine that cannot be absorbed by the bossing portion is absorbed by the absorbent body of the main absorbent article. In such cases, the absorption speed of the pulp in the absorbent body of the main absorbent article cannot keep up with the flow of the body fluid, and there is a problem in that the body fluid easily flows to outside of both left and right sides of the absorbent article.

SUMMARY OF THE INVENTION

The present invention has been made in order to solve the abovementioned problems and has as an object the provision of an absorbent article in which body fluid does not remain on a top sheet even when large quantities of the body fluid are received, and in which the body fluid can assuredly be captured without leaking to the outside.

In order to solve the abovementioned problems, the present inventors found that, by widely diffusing the body fluid on the top sheet, urine does not remain on the surface but can move quickly to the absorbent body, and thus the present invention was realized. Specifically, the present invention provides an evagination means on which an elastic member is arranged, in an absorbent article provided with an absorbent body and a top sheet, and by arranging a region that is not attached to other constituent members on the top sheet, many inflected creases occur due to a contraction force on the top sheet, and the body fluid can move in these creases. More specifically, the present invention provides the following.

In a first aspect of the present invention, an absorbent article of an elongated shape having a longitudinal direction and a lateral direction, is provided with a fluid permeable top sheet, a fluid impermeable back sheet, an absorbent body, disposed between the top sheet and the back sheet, for absorbing and retaining body fluid, and an evagination means arranged on a strip along a center line in the longitudinal direction of the absorbent article, between the top sheet and the absorbent body, near the center line of the top sheet, wherein the evagination means includes a fluid permeable member comprising a fixing portion that is fixed to the absorbent body and forms the main part of the evagination means, a top face portion for supporting the top sheet, and an uprising portion that links the fixing portion and the top face portion and stands up in a direction towards the body when worn, the top face portion has a plurality of elastic members disposed so as to extend in the longitudinal direction parallel to the center line of the absorbent article, and the top sheet has an unattached region from the center line of the top face portion to between both side edges of the absorbent article.

According to the first aspect of the invention, many inflected creases occur on the top sheet. That is, according to the present invention, between the center portion in the longitudinal direction of the evagination means and the side edge portions of the absorbent article, the top sheet is not attached to other constituent members, and is in a free state. Here, in the portion in which the elastic member is disposed, the evagination means contracts due to shrinkage stress, and the shrinkage stress also acts on the top sheet, in the portion attached to this evagination means. Consequently, in the top sheet, creases occur parallel to the lateral direction in a portion located above the evagination means. On the other hand, between the side edge portions and the evagination means, a portion of the top sheet attached to the evagination means, which contracts, and a portion of the top sheet attached to the side edge portions, which does not contract, react so that diagonal creases occur. In this way, creases that run diagonally to the front-rear direction and creases that are parallel to the lateral direction in the top sheet occur, and the body fluid received by the top sheet is diffused in these creases and conducted quickly to the absorbent body.

In this point, in conventional absorbent articles, an arrangement of an unattached region between the top sheet and the absorbent body has not been considered. For example, Japanese Unexamined Patent Application Publication No. 2002-320638 discloses an embodiment in which a bossing portion is formed by folding an absorbent top sheet, but an exposed portion that is not folded is attached to the entire top sheet. Accordingly, with regard to a surface touching the body, there is almost no region not attached anywhere to the top sheet. As a result, there is little occurrence of creases due to arranging the bossing portion, and creases in the diagonal direction do not easily occur.

Furthermore, even if the bossing portion is provided with an elastic portion as in Japanese Patent No. 3442929, since a region that is not attached to the top sheet is not present, creases due to expanding and contracting material in the bossing portion only occur in a lateral direction, and diagonal creases as in the present invention do not easily occur. As a result, a large amount of body fluid accumulate at both side edges of the bossing portion; in addition, absorption in areas outside of the bossing portion do not keep pace with the speed of flow of the body fluid, and it is difficult to quickly diffuse and capture urine as in the present invention.

In contrast, in the present invention, even with a large amount of body fluid, the body fluid is passed to the creases on the top sheet that receives the fluid and is quickly diffused. In this way, the body fluid does not accumulate in the top sheet, nor is the body fluid concentrated in one spot only so that the absorption capability of the absorbent body becomes saturated in that portion and leakage occurs.

Moreover, since creases occur easily in the top sheet, the top sheet is preferably not fitted on in a taut state but rather is fitted on with a degree of slack.

In a second aspect of the invention, in the absorbent article according to the first aspect of the invention, in the unattached region, creases occur in a diagonal direction from the top face portion towards both side edges.

According to the second aspect of the invention, the creases occur in a diagonal direction on the top sheet. As a result, the crease do not only occur in a lateral direction as in the conventional art, and it is possible to prevent situations in which the body fluid can only diffuse at both sides of the body fluid excretion portion.

In a third aspect of the invention, in the absorbent article according to the first aspect of the invention, the top sheet includes a first attachment region that is attached to the top face portion, and second attachment regions for fixing along and close to both side edges in the longitudinal direction of the absorbent article, wherein the width is adjusted in the lateral direction of the first attachment region in order to change an angle, with respect to the lateral direction, of the creases in a diagonal direction, that occur from the top face portion towards both side edges, from the first attachment region to between the second attachment regions.

According to the third aspect of the invention, by suitably adjusting the attachment region of the top face portion and the top sheet that is the first attachment region, the angle of the creases that occur in the top sheet can be adjusted. For example, if the first attachment region is widened, the diagonal angle of the creases can be made tighter overall, and if the first attachment region is narrowed, the angle of the creases can be loosened.

In a fourth aspect of the invention, the absorbent article according to the first aspect of the invention includes a leakage prevention means arranged along and in the vicinity of both side edges in the longitudinal direction of the absorbent article, wherein the top sheet includes a first attachment region attached to the top face portion, and second attachment regions for fixing along and in the vicinity of both side edges in the longitudinal direction of the absorbent article so as to make the leakage prevention means of the absorbent article function.

According to the fourth aspect of the invention, the leakage prevention means is arranged as, for example, side gathering regions described below, along and in the vicinity of both sides of the absorbent article. In this way, body fluid such as urine, excreted in a large amount, is prevented from leaking to the outside, from both side edges in the longitudinal direction of the absorbent article. The second attachment regions of the top sheet are disposed along and in the vicinity of both side edges in the longitudinal direction of the absorbent article, without damaging the capability of the abovementioned side gathering regions, for example, near the base of the side gathering regions. That is, it is important that the second attachment regions of the top sheet be arranged so as to smoothly conduct body fluid held back by the side gathering regions to the absorbent body via the top sheet and the evagination means.

In a fifth aspect of the invention, in the absorbent article according to the fourth aspect of the invention, the second attachment regions of the top sheet are arranged along regions formed in the leakage prevention means.

In a sixth aspect of the invention, in the absorbent article according to the fifth aspect of the invention, the second attachment regions of the top sheet are attached to the fixed portions linked to the absorbent body.

In a seventh aspect of the invention, in the absorbent article according to the fifth aspect of the invention, the second attachment regions of the top sheet are attached to the back sheet.

According to the invention as described in one of the fifth, sixth, or seventh aspects of the invention, the second attachment regions of the top sheet may be disposed so as to smoothly conduct body fluid held back by the side gathering regions that are the leakage prevention means, to the absorbent body via the top sheet and the evagination means.

In an eighth aspect of the invention, in the absorbent article according to the first aspect of the invention, the top sheet includes a first attachment region attached to the top face portion, and second attachment regions attached to the fixed portion linked to the absorbent body in the vicinity of both side edges in the longitudinal direction of the absorbent article.

In a ninth aspect of the invention, in the absorbent article according to the first aspect of the invention, the top sheet includes a first attachment region attached to the top face portion, and second attachment regions attached to the back sheet in the vicinity of both side edges in the longitudinal direction of the absorbent article.

According to the eighth or ninth aspects of the invention, creases that form a base for the top sheet on the top face portion are formed by an elastic member on the top face portion. The top sheet is not attached to other constituent members, from the first attachment region to between the second attachment regions, and is in a free state. In this way, in the top sheet, the creases that form the abovementioned base develop into creases that extend diagonally towards the second attachment regions. That is, the second attachment regions in the top sheet fix the side edge portions of the top sheet and contribute to the occurrence of the diagonal creases extending from the first attachment region.

According to the present invention, by arranging a free portion not attached to anywhere on the top sheet, between the attachment region of the top sheet and the top face portion of the evagination means, and the attachment region of the top sheet and both side edge portions, the creases are formed diagonally on the top sheet. By the excreted body fluid passing along these creases, the body fluid can be guided (diffused) to the front, back, and both sides of the excretion portion, and can be guided to the absorbent body positioned below the top sheet, to be absorbed.

Moreover, since absorbing points are increased by the diffusion of the body fluid, even in cases in which a large amount of body fluid is excreted, since the body fluid is quickly diffused in front, rear, and diagonal directions, to be absorbed, the amount of body fluid accumulating on the surface can be reduced and leakage to the outside can be prevented. In addition, since by the absorbing area increasing, leeway can be realized in absorptive capacity per unit of area, the amount of wetback body fluid (back flow) can be reduced.

DETAILED DESCRIPTION OF THE INVENTION

An example of a preferred embodiment of the present invention is explained below, referring to the figures.

Figure 1:
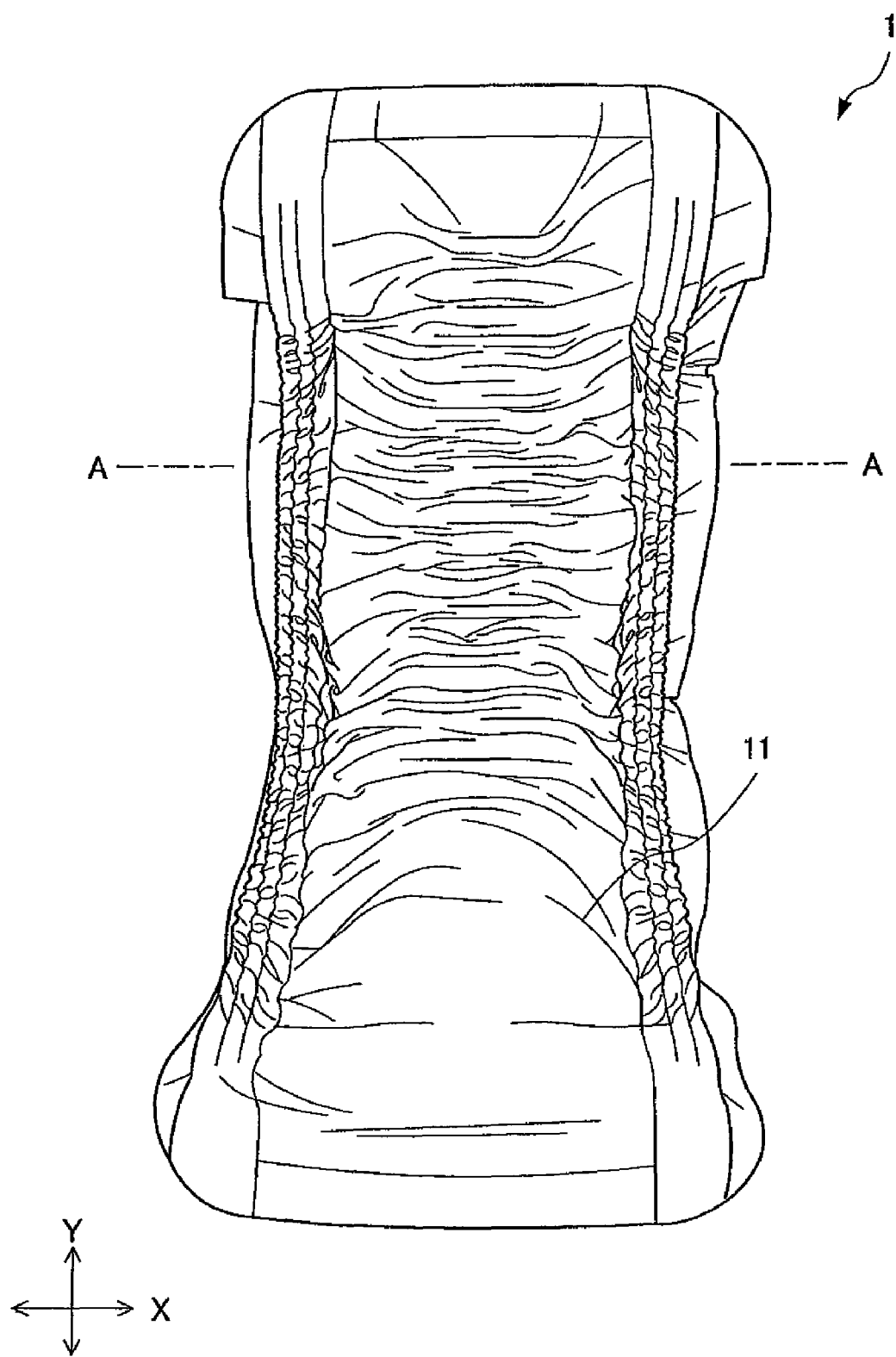
FIG. 1 is a front view of an absorbent article related to a first embodiment.
Figure 2:
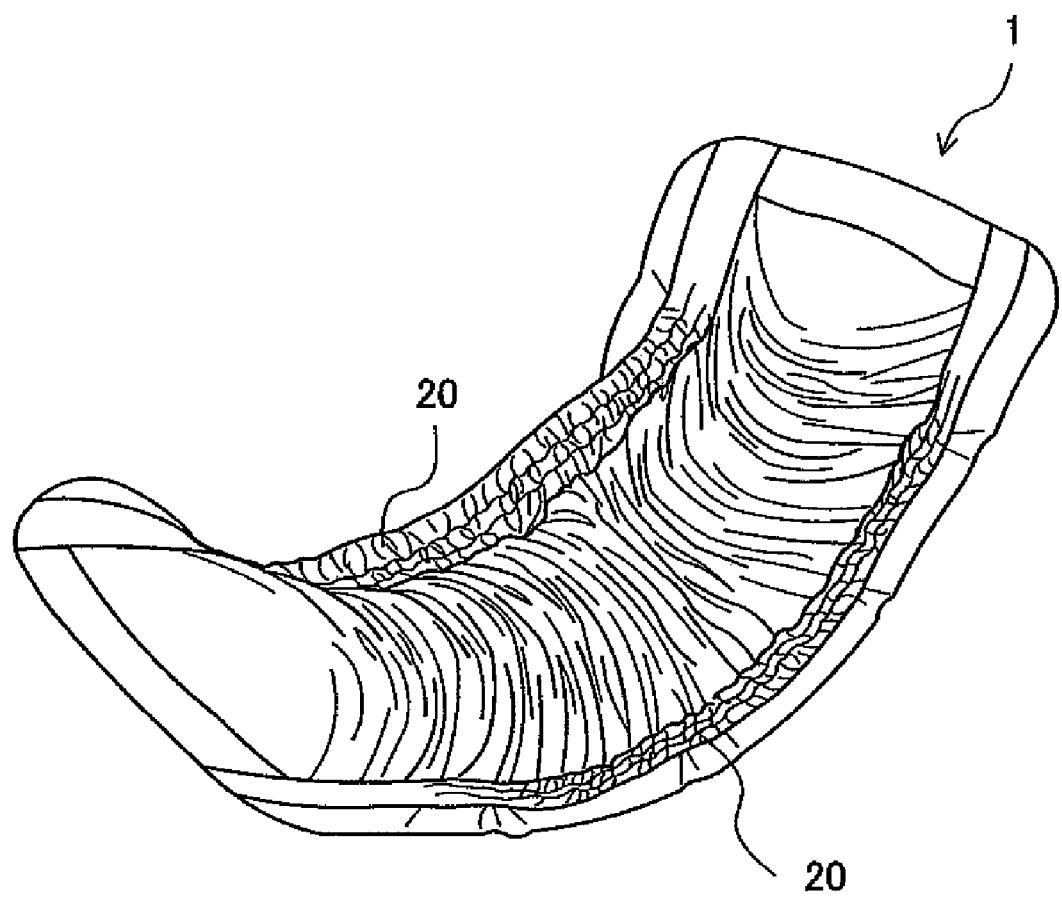
FIG. 2 is a perspective view of the absorbent article related to the first embodiment.
Figure 3:
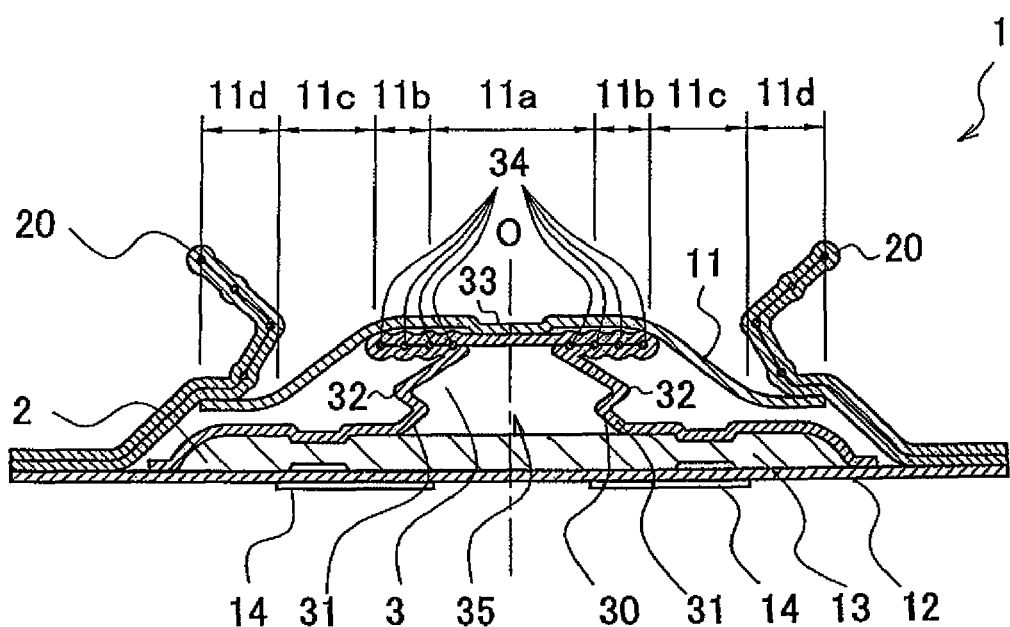
FIG. 3 is a cross-sectional view cut at A-A in FIG. 2.
Figure 4:
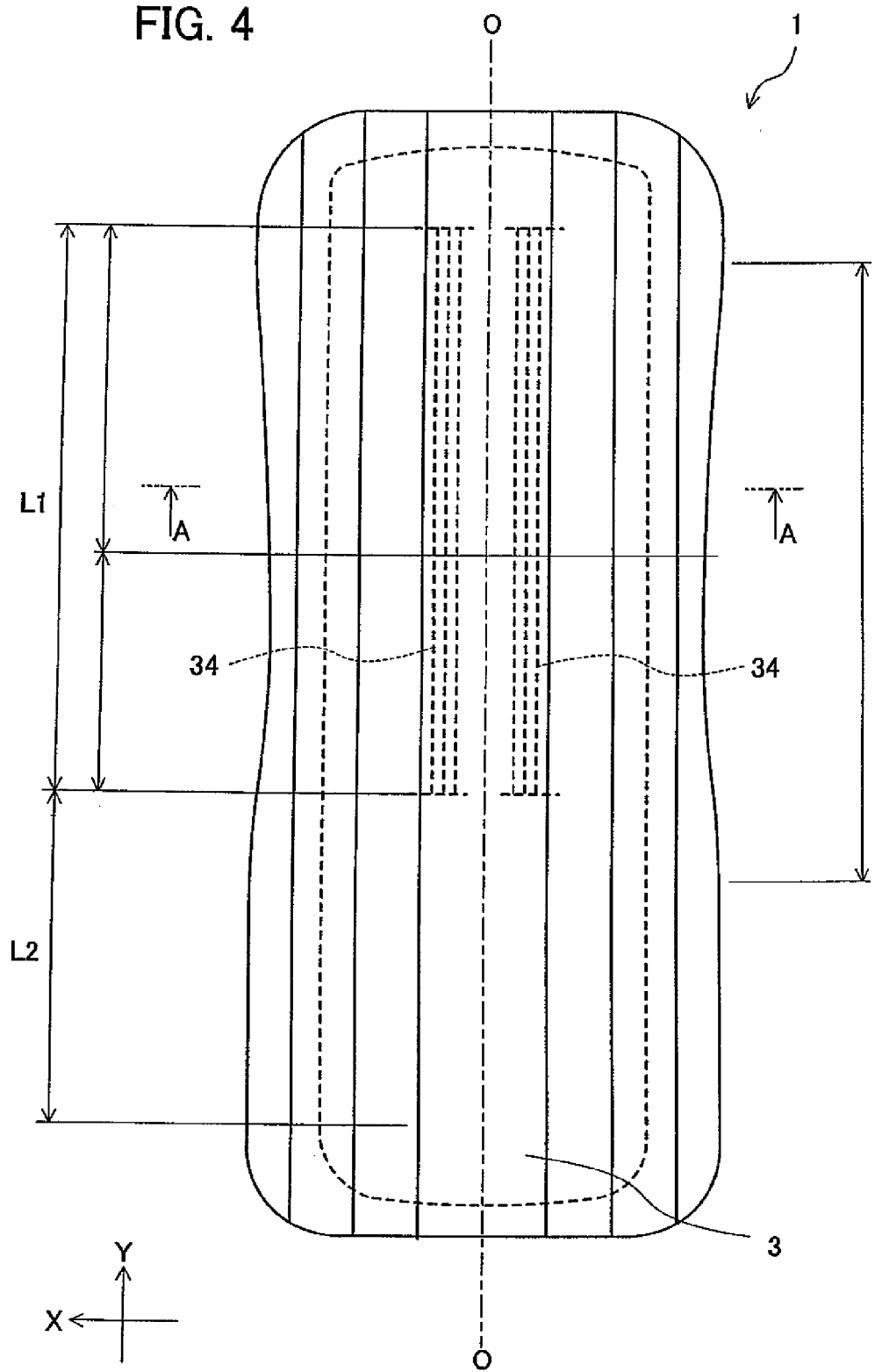
FIG. 4 is a front view showing a state in which the absorbent article related to the first embodiment is opened in a planar form.

FIG. 1 is a front view showing an absorbent article related to the present embodiment, FIG. 2 is a perspective view, FIG. 3 is a cross-sectional view, and FIG. 4 is a front view opened in a planer form.

Overall Composition

As shown in FIG. 1, the absorbent article of the present embodiment is composed so that, in order to quickly diffuse excreted urine, many inflected creases occur in a top sheet 11 that touches the body. As a result, even when a relatively large amount of urine is excreted at one time due to urgent incontinence, a capability can be realized to diffuse and absorb the urine. In addition, as shown in FIG. 2, an absorbent article 1 is easily fitted on by a wearer, and has concave curved shapes sunk into a fluid receiving face so that leakage do not easily occur.

This absorbent article 1 has an elongated shape in which the length dimension in a longwise direction that is a longitudinal direction (Y direction) is longer than the dimension in a width direction (X direction) that is a lateral direction; the length dimension in the longitudinal direction is of the order of 300 to 500 mm, and the dimension in the lateral direction is of the order of 100 to 200 mm. In addition, in a state in which the article is fitted between the body and underclothing, the thickness thereof is of the order of 5 to 30 mm.

As shown in FIG. 3, the absorbent article 1 includes a fluid permeable top sheet 11, a fluid impermeable back sheet 12, and an absorbent body 13 disposed between the top sheet 11 and the back sheet 12, for absorbing and retaining body fluid. Furthermore, an evagination means 3 is provided formed from a fluid permeable sheet 30 arranged extending along a center line O in a longitudinal direction of a supporting body 2 formed from the absorbent body 13.

Evagination Means

The evagination means 3 is formed in a single line from the fluid permeable sheet 30, and is composed of a fixing portion 31 fixed to the supporting body 2, uprising portions 32 that make the evagination means rise, and a top face portion 33 for causing close attachment to the body when worn.

As shown in FIG. 3, both sides of the fluid permeable sheet 30 that sandwich the longitudinal direction center line O are each folded in two; elastic members 34 are sandwiched between the folded fluid permeable sheet 30; and folded inner faces of fluid permeable sheet 30 and the elastic members 34 are attached and fixed by a hot melt type adhesive. The elastic members 34 straddle the longitudinal direction center line O, four members thereof being arranged on one side and four members on the other side, and being fixed to the fluid permeable sheet 30 in a state in which they are extended by a factor of from 1.2 to 2, in the longitudinal direction. A central gathering region is formed by the contraction force of these elastic members 34, so that the upright portions 32 rise.

These elastic members 34 are not disposed over the whole longitudinal direction of the evagination means 3, but, as shown in FIG. 4, are disposed only in a first region L1, and are not disposed in a second region L2 to the rear thereof. Moreover, in the present embodiment, the length dimension of the first region L2 is of the order of 130 to 230 mm, and the length dimension of the second region L2 is arranged to be shorter that the length dimension of the first region L1. Furthermore, the length dimensions of the first region L1 and the second region L2 may be the same, or the second region L2 may have a longer dimension.

As shown in FIG. 3, the fluid permeable top sheet 11 is provided on the top face of the fluid-receiving side of the evagination means 3, the elastic members 34 cover the fluid receiving side of the top face portion 33, and the top sheet 11 and the top face portion 33 are attached at a first attachment region 11a. Second attachment regions 11d are arranged along the side gathering regions 20 formed as a leak preventing means. Here, at the second attachment regions 11d, the top sheet 11 is attached to the side gathering regions 20 that are the leak prevention means positioned at both side edges in a longitudinal direction of the absorbent body 13, with the absorbent body 13 positioned thereunder. Furthermore, in the top sheet 11 there are also an unattached region 11b and an unattached region 11c in a free state, not attached to any other places.

Here, since there is no elastic member in the second attachment region 11d, the top sheet 11 stays extended. Conversely, in the attachment region 11a attached to the top face portion, during usage, the top sheet 11 contracts with the top face portion 33, and parallel creases in a lateral direction the same as before occur in the first attachment region 11a. In the composition of the present invention, in the unattached regions 11b and 11c between the first attachment region 11a attached to this top face portion 33 and the second attachment regions 11d attached to both side edges of the absorbent body 13, stretched diagonal creases occur with the contractions of the elastic members 34 of the top face portion 33. This is due to the fact that, since the free portion of the top sheet 11 is not affected by contraction in the second attachment regions 11d but the first attachment region 11a is affected by the contraction, the creases occur diagonally in the unattached regions 11b and 11c that are free regions positioned therebetween.

Moreover, with regard to the contraction of the top face region 33, there is a contraction area that contracts from both a position where an effect of the elastic member 34 is first received and a position where it is last received, towards a center portion. As a result, contracting distance becomes longer from the center portion of the contraction area to more faraway locations. Accordingly, in the unattached regions 11b and 11c, the creases occur parallel to the lateral direction of the top face region in the portion above the parallel lines of the central portion of the contraction region, the diagonal creases occur according to distance from above the parallel lines of the central portion of the contraction region, and since movement distance of the top sheet 11 becomes longer with distance, the angle of the diagonal creases becomes sharper.

With this type of crease angle, for example, if the area of the first attachment region 11a is widened, the diagonal angle overall becomes sharper, and conversely, if the area of the first attachment region 11a is narrowed, it becomes less sharp. Moreover, a preferable area of the attachment area of the top face region 33 and the top sheet 11 is at most an area of the same range as the width of the top face region 33, and at least about one third of the width of the top face region 33 (in such a case, the width dimension of the top face region 33 is preferably in a range half or less of a distance between support points of the side gathering region 20. Here, in cases in which the attachment width is wider than the abovementioned maximum range, since the distance from the attachment position to each of the left and right side gathering regions 20 becomes too short, the creases do not easily occur. Conversely, in cases in which the attachment width is narrower than the abovementioned minimum range, the attachment width with the top sheet 11 narrows, so that body fluid absorption and permeation efficiency worsen.

In this way, by the creases that occur in the fluid permeable top sheet, the excreted urine while passing through the top sheet 11 runs along the creases that occur in the top face and flows in a diagonal direction to the front and rear. The urine that flows in a diagonal direction to the front and rear, while passing through the fluid permeable top sheet, reaches the side gathering regions 20, and is absorbed by the absorbent body 13. The urine that passes through the fluid permeable top sheet 11 before reaching the side gathering regions 20 is absorbed at a central area of the absorbent body 13. As a result, even in cases in which a large quantity of urine is excreted, since the urine is quickly dispersed, and the urine does not stay on the surface, wearability is excellent, and since the urine is guided so as to be assuredly absorbed in the absorbent body, the absorbent article 1 has high leakage prevention effects.

Component Members

Top Sheet

The top sheet 11 is hydrophilic and has a capability of being permeable to fluids. It is preferably formed of hydrophilic synthetic resin fiber, and natural fiber such as pulp having fluid retaining capability, but not including resin with high water absorbing capability, and water-absorbing resin such as polyvinyl alcohol (PVA). Through-air non-woven fabric, with a weight in a range of 10 to 40 g/m$^2$ that can exhibit excellent fluid permeable capability, is preferably used. The through-air non-woven fabric is formed with a core of polypropylene resin (PP) or polyethylene terephthalate resin (PET), and with core-in-sheath composite synthetic fiber with a sheath of polyethylene resin (PE), or PET fiber, PP fiber, or the like. Furthermore, it may also be formed of a resin film having many fluid permeable pores.

The top sheet 11 is given an uneven shape by bossing processing, so as to contract in at least one of a longitudinal direction and a lateral direction. The bossing processing is carried out by cutting into the non-woven fabric and resin film between pairs of rolls having an uneven surface. By undergoing this process, the top sheet 11 has a capability of contracting in at least one of the longitudinal and the lateral direction. As a result, the evagination means 3 that covers the top sheet 11 can rise up easily from the surface of the absorbent body 13, and the evagination means 3 can move relatively freely to the left and right with the top sheet 11. Furthermore, the top sheet 11 is formed of non-woven fabric including elastically contractible fiber such as polyurethane fiber or the like, and the top sheet 11 may have elastic contractibility.

Back Sheet

As shown in FIG. 3, a back sheet 12 is arranged on the clothing side of the absorbent article 1. The external shape of the back sheet 12 is the same as the external shape of the absorbent article 1 shown in FIG. 2. This back sheet 12 is formed of polyethylene resin film such as fluid impermeable and non-ventilating resin film. Moreover, the back sheet 12 may be formed by fluid impermeable and ventilating resin film.

A pressure sensitive adhesive layer 14 is provided on the external face of the back sheet 12. This pressure sensitive adhesive layer 14 is formed by applying a rubber-based hot melt type adhesive or the like. Although omitted from FIG. 3 and FIG. 4, a removable sheet is attached to the surface of the pressure sensitive adhesive layer 14 until the absorbent article 1 is used, to protect the pressure sensitive adhesive layer 14.

Absorbent Body

An absorbent body 13 is set on the back sheet 12, and the back sheet 12 and the absorbent body 13 are attached and fixed by a hot melt adhesive or the like. The absorbent body 13 is a mixture of pulp fiber and highly water-absorbent resin, the included proportion of the highly water absorbent resin being of the order of 20 to 60% mass, and the total weight of the pulp fiber and the highly water absorbent resin being of the order of 500 to 2000 g/m$^2$, but this figure does not imply a limitation thereto. The absorbent body 13 has, on a lower layer absorbent body in which pulp fiber and highly water absorbent resin are mixed, an upper layer absorbent body in which pulp fiber and highly water absorbent resin are mixed, and includes hydrophilic tissue paper.

Evagination Means

A fluid permeable sheet 30 is provided on the surface of the fluid receiving side of the absorbent body 13. This fluid permeable sheet 30 is hydrophilic and has a capability of allowing fluid to pass through. The fluid permeable sheet 30 is preferably formed of hydrophilic-processed synthetic resin fiber, and includes natural fiber such as pulp having fluid retaining capability, but not including resin with high water absorbing capability, and water-absorbing resin such as polyvinyl alcohol (PVA). Through-air non-woven fabric, with a weight in a range of 10 to 40 g/m$^2$, that can exhibit excellent fluid permeable capability, is preferably used. The through-air non-woven fabric is formed with a core of polypropylene resin (PP) or polyethylene terephthalate resin (PET), and with core-in-sheath composite synthetic fiber with a sheath of polyethylene resin (PE), or PET fiber, PP fiber, or the like. However, the fluid permeable sheet 30 may also be formed to include the pulp fiber, rayon fiber or the like.

Figure 5:
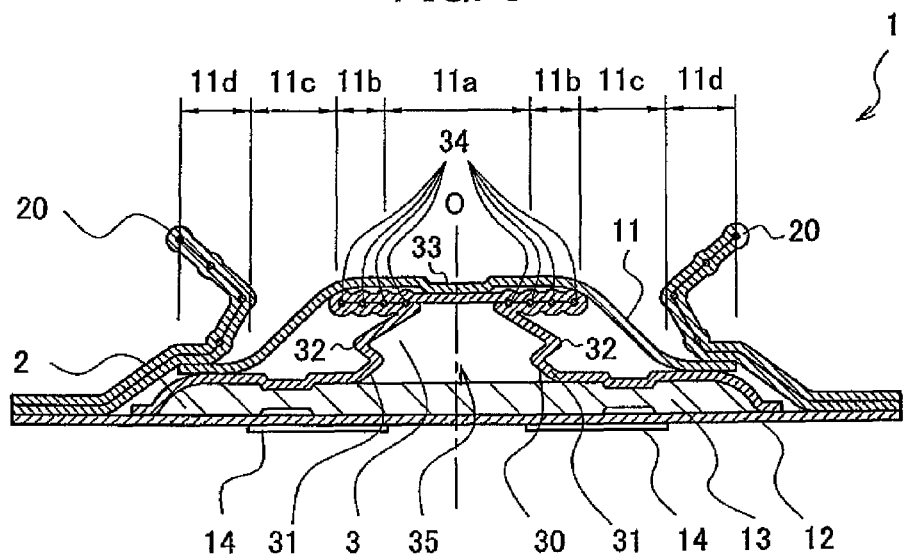
FIG. 5 is a cross-sectional view showing a first modified example of FIG. 3.

FIG. 5 is a sectional view showing a first modified example of FIG. 3. The form of the second attachment region 11d in the top sheet 11 is different compared to FIG. 3. In the second attachment regions 11d, the top sheet 11 is attached to the side gathering region 20 that is a leakage prevention means positioned at both side edges in the longitudinal direction of the absorbent body 13. In this way, the second attachment regions 11d are not easily affected by movement of the side gathering regions 20, and a stronger attachment is realized. Also in this type of structure, functions of the side gathering regions 20 are not damaged, and the second attachment regions 11d in the top sheet 11 fix the side edge regions of the top sheet 11, and also contribute to the generation of the diagonal creases extending from the first attachment region 11a.

Figure 6:
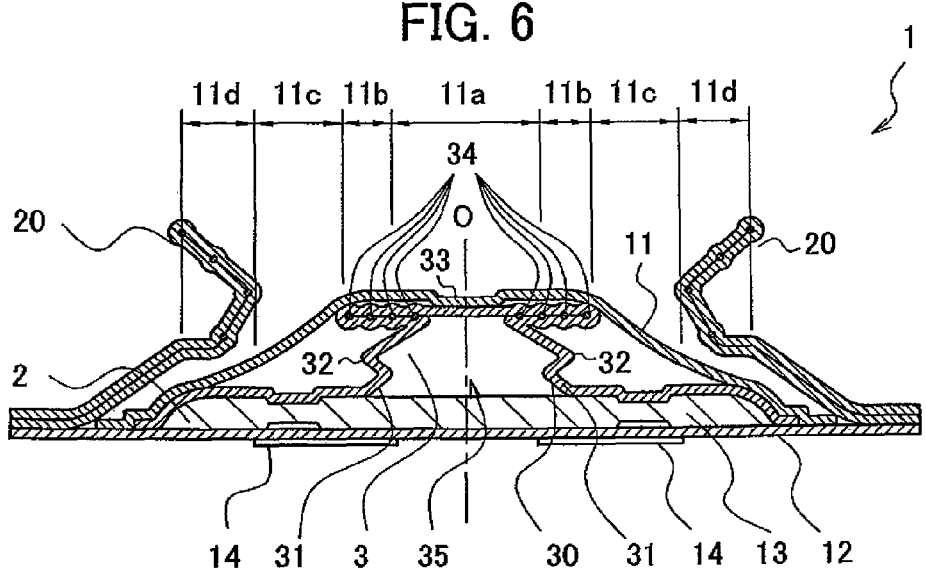
FIG. 6 is a cross-sectional view showing a second modified example of FIG. 3.

FIG. 6 is a sectional view showing a second modified example of FIG. 3. The form of the second attachment region 11d in the top sheet 11 is different compared to FIG. 3. In the second attachment region 11d, the top sheet 11 is attached to the back sheet 12. Furthermore, in the second attachment region 11d, in addition, a fixed portions 31 may also be attached at the side edge region. In this way, the second attachment regions 11d are not easily affected by movement of the side gathering regions 20, and attachments are realized in which the range in which the creases are formed is enlarged. Also in this type of structure, the second attachment regions 11d in the top sheet 11 fix the side edge regions of the top sheet 11, and also contribute to the generation of the diagonal creases extending from the first attachment region 11a.

While preferred embodiments of the present invention have been described and illustrated above, it is to be understood that they are exemplary of the invention and are not to be considered to be limiting. Additions, omissions, substitutions, and other modifications can be made thereto without departing from the spirit or scope of the present invention. Accordingly, the invention is not to be considered to be limited by the foregoing description and is only limited by the scope of the appended claims.

What is claimed is:

1. An absorbent article of an elongated shape having a longitudinal direction and a lateral direction, said article comprising:
   a fluid permeable top sheet;
   a fluid impermeable back sheet;
   an absorbent body, disposed between the top sheet and the back sheet, for absorbing and retaining body fluid; and
   a fluid permeable member comprising hydrophilically-processed synthetic resin fibers without water-absorbent resin and arranged along the longitudinal direction of the absorbent article, between the top sheet and the absorbent body;
   leakage prevention barriers arranged along and in vicinity of the longitudinal side edges of the absorbent article, respectively,
   wherein
   the fluid permeable member comprises:
      a fixed portion that is directly fixed to the absorbent body,
      a top face portion directly supporting the top sheet from below and along a longitudinal center line of the article, and
      an uprising portion that links the fixed portion and the top face portion and stands up in a thickness direction of the article upwardly from the absorbent body,
   the top face portion has a plurality of elastic members directly attached thereto so as to extend in the longitudinal direction parallel to the longitudinal center line of the absorbent article, and
   the top sheet has:
      a first attachment region that is directly attached to the top face portion along the longitudinal center line of the absorbent article,
      an unattached region that extends from longitudinal side edges of the top face portion toward respective longitudinal side edges of the absorbent article while being upwardly spaced from the absorbent body, and
      second attachment regions where the side edges of the top sheet extending in the longitudinal direction are positioned between the leakage prevention barriers and the absorbent body, respectively, in vicinity of the longitudinal side edges of the absorbent article,
   wherein the leakage prevention barriers have elasticized edges risable above, along and in vicinity of the longitudinal side edges of the absorbent article, respectively, and
   wherein the second attachment regions of the top sheet are formed below the elasticized edges of the leakage prevention barriers.

2. The absorbent article according to claim 1, wherein said fluid permeable member continuously extends in the lateral direction across the longitudinal center line of the absorbent article.

3. The absorbent article according to claim 2, wherein in the unattached region of the top sheet, creases occur in a diagonal direction from the top face portion towards the side edges of the article.

4. The absorbent article according to claim 2, wherein the top sheet is fixed to the article along and in vicinity of the longitudinal side edges of the absorbent article at the second attachment regions;
   wherein a width of the first attachment region is adjusted in the lateral direction in order to change an angle, with respect to the lateral direction, of creases that occur in the unattached region of the top sheet in a diagonal direction from the first attachment region to the second attachment regions.

5. The absorbent article according to claim 2, wherein the second attachment regions of the top sheet are directly attached to the leakage prevention barriers, respectively.

6. The absorbent article according to claim 2, wherein the second attachment regions of the top sheet are directly attached to the back sheet.

7. The absorbent article according to claim 2, wherein the second attachment regions are directly attached to the fixed portion of the fluid permeable member in vicinity of the longitudinal side edges of the absorbent article.

8. The absorbent article according to claim 2, wherein the second attachment regions are directly attached to the back sheet in vicinity of the longitudinal side edges of the absorbent article.

9. The absorbent article according to claim 2, wherein the elastic members are located (i) directly below a central region of the top sheet being supported by the top face portion, and (ii) on opposite sides of the first attachment region as seen in the lateral direction.

10. The absorbent article according to claim 9, wherein areas of the top face portion, where the elastic members are directly bonded to, are contactable with the overlying top sheet without being directly attached to the top sheet.

11. The absorbent article according to claim 6, wherein the top sheet is entirely spaced inwardly in the lateral direction from the leakage prevention barriers.

12. The absorbent article according to claim 2, wherein the absorbent body comprises a mixture of pulp fiber and water-absorbent resin.

13. The absorbent article according to claim 12, wherein the fluid permeable member is free of water-absorbent resin.

14. The absorbent article according to claim 12, wherein the fluid permeable member is a sheet of hydrophilic nonwoven fabric.

15. The absorbent article according to claim 2, wherein the elastic members extend in the longitudinal direction for less than a full length of the absorbent body.

16. The absorbent article according to claim 2, wherein a width of the first attachment region in the lateral direction is between one third and a half of that of the top face portion.

17. The absorbent article according to claim 1, wherein the top face portion has a lower surface directly attached to an upper surface of the uprising portion, and the elastic members are directly sandwiched between and bonded to the lower surface of the top face portion and the upper surface of the uprising portion.

18. The absorbent article according to claim 1, wherein the second attachment regions of the top sheet are also directly attached to the fixed portion of the fluid permeable member.

19. An absorbent article of an elongated shape having a longitudinal direction and a lateral direction, said article comprising:
   a fluid permeable top sheet;
   a fluid impermeable back sheet;
   an absorbent body, disposed between the top sheet and the back sheet, for absorbing and retaining body fluid; and
   a fluid permeable member comprising hydrophilically-processed synthetic resin fibers without water-absorbent resin and arranged along the longitudinal direction of the absorbent article, between the top sheet and the absorbent body, said fluid permeable member continuously extending in the lateral direction across a longitudinal center line of the absorbent article; and
   leakage prevention barriers arranged along and in vicinity of the longitudinal side edges of the absorbent article, respectively,
   wherein
   the fluid permeable member comprises:
      a fixed portion that is directly fixed to the absorbent body,
      a top face portion directly supporting the top sheet from below and along the longitudinal center line of the article, and
      an uprising portion that links the fixed portion and the top face portion and stands up in a thickness direction of the article upwardly from the absorbent body,
   the top face portion has a plurality of elastic members directly attached thereto so as to extend in the longitudinal direction parallel to the longitudinal center line of the absorbent article, and
   the top sheet has:
      a first attachment region that is directly attached to the top face portion along the longitudinal center line of the absorbent article, and
      an unattached region that extends from longitudinal side edges of the top face portion toward respective longitudinal side edges of the absorbent article while being upwardly spaced from the absorbent body, and
   second attachment regions where the side edges of the top sheet extending in the longitudinal direction are positioned between the leakage prevention barriers and the absorbent body, respectively, in vicinity of the longitudinal side edges of the absorbent article,
   wherein the second attachment regions of the top sheet are directly attached to the leakage prevention barriers, respectively, and
   wherein the second attachment regions of the top sheet are also directly attached to the fixed portion of the fluid permeable member.

20. An absorbent article of an elongated shape having a longitudinal direction and a lateral direction, said article comprising:
   a fluid permeable top sheet;
   a fluid impermeable back sheet;
   an absorbent body, disposed between the top sheet and the back sheet, for absorbing and retaining body fluid; and
   a fluid permeable member comprising hydrophilically-processed synthetic resin fibers without water-absorbent resin and arranged along the longitudinal direction of the absorbent article, between the top sheet and the absorbent body, said fluid permeable member continuously extending in the lateral direction across a longitudinal center line of the absorbent article; and
   leakage prevention barriers arranged along and in vicinity of the longitudinal side edges of the absorbent article, respectively,
   wherein
   the fluid permeable member comprises:
      a fixed portion that is directly fixed to the absorbent body,
      a top face portion directly supporting the top sheet from below and along the longitudinal center line of the article, and
      an uprising portion that links the fixed portion and the top face portion and stands up in a thickness direction of the article upwardly from the absorbent body,
   the top face portion has a plurality of elastic members directly attached thereto so as to extend in the longitudinal direction parallel to the longitudinal center line of the absorbent article, and
   the top sheet has:
      a first attachment region that is directly attached to the top face portion along the longitudinal center line of the absorbent article, and
      an unattached region that extends from longitudinal side edges of the top face portion toward respective longitudinal side edges of the absorbent article while being upwardly spaced from the absorbent body, and
   second attachment regions where the side edges of the top sheet extending in the longitudinal direction are positioned between the leakage prevention barriers and the absorbent body, respectively, in vicinity of the longitudinal side edges of the absorbent article,
   wherein the second attachment regions of the top sheet are directly attached to the leakage prevention barriers, respectively, and
   wherein the top sheet is entirely spaced upwardly from the absorbent body due to the direct attachment of the first and second attachment regions to the top face portion and the leakage prevention barriers, respectively.

* * * * *